(12) United States Patent
Wildsmith et al.

(10) Patent No.: US 7,123,985 B2
(45) Date of Patent: Oct. 17, 2006

(54) DESIGN BUILD TEST CYCLE REDUCTION

(75) Inventors: Christopher Wildsmith, Jacksonville, FL (US); Victor Lust, Jacksonville, FL (US); Jose L. Perez, Jacksonville, FL (US); Krish Damodharan, Jacksonville, FL (US); Jeffrey M. Roy, Boulder, CO (US); Jason Daniel, Liberty Township, OH (US); David F. Pinella, Loveland, OH (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 202 days.

(21) Appl. No.: 10/410,802

(22) Filed: Apr. 10, 2003

(65) Prior Publication Data

US 2004/0075809 A1    Apr. 22, 2004

Related U.S. Application Data

(60) Provisional application No. 60/372,738, filed on Apr. 12, 2002.

(51) Int. Cl.
*B29C 39/00* (2006.01)
(52) U.S. Cl. ...................... 700/197; 264/1.32
(58) Field of Classification Search ............... 700/197, 700/200, 204, 182; 264/1.32, 25
See application file for complete search history.

(56) References Cited

U.S. PATENT DOCUMENTS

| | | | |
|---|---|---|---|
| 4,669,466 A | 6/1987 | L'Esperance | |
| 4,721,379 A | 1/1988 | L'Esperance | |
| 5,067,067 A | 11/1991 | Estelle et al. | |
| 5,452,031 A * | 9/1995 | Ducharme | 351/177 |
| 5,475,452 A | 12/1995 | Kuhn et al. | |
| 5,502,518 A | 3/1996 | Lieberman | |
| 5,724,258 A | 3/1998 | Roffman | |
| 5,737,056 A | 4/1998 | Martin et al. | |
| 5,764,343 A | 6/1998 | Tanaka | |
| 5,805,348 A | 9/1998 | Estelle et al. | |
| 5,861,114 A | 1/1999 | Roffman et al. | 264/2.5 |
| 5,880,809 A | 3/1999 | Lieberman et al. | |
| 5,953,098 A | 9/1999 | Lieberman et al. | |
| 5,969,790 A | 10/1999 | Onufryk | |
| 6,046,745 A | 4/2000 | Moriya et al. | |

(Continued)

OTHER PUBLICATIONS

U.S. Appl. No. 60/313,808, filed Aug. 2001, Andino et al.*

(Continued)

*Primary Examiner*—Leo Picard
*Assistant Examiner*—Chad Rapp
(74) *Attorney, Agent, or Firm*—Joseph Kincart

(57) ABSTRACT

An ophthalmic lens design and modeling system comprises a user interface providing functionality for generating a template associated with a desired lens design to be manufactured, the template comprising design information sufficient for generating three-dimensional (3D) models of lens, and 3D models of associated components required for lens manufacture in an ophthalmic lens manufacturing system. The system further includes functionality for generating and/or specifying linking information, via the user interface, that governs the physical behavior of lens design features included in said template in accordance with one or more process parameters affecting lens manufacture and manufacture of associated components in an ophthalmic lens manufacturing system. The use of the template and design and linking information therein thus facilitates rapid lens modeling and lens manufacturing operations with greater accuracy, thereby reducing lens design build and test (DBT) cycle time.

34 Claims, 9 Drawing Sheets

U.S. PATENT DOCUMENTS

| | | | |
|---|---|---|---|
| 6,089,711 | A | 7/2000 | Blankenbecler et al. |
| 6,149,609 | A | 11/2000 | Lieberman et al. |
| 6,241,355 | B1 | 6/2001 | Barsky |
| 6,271,914 | B1 | 8/2001 | Frey et al. |
| 6,338,559 | B1 | 1/2002 | Williams et al. |
| 6,340,229 | B1 | 1/2002 | Lieberman et al. |
| 6,464,355 | B1 | 10/2002 | Gil |
| 2003/0050726 | A1* | 3/2003 | Jaffrey .................. 700/182 |
| 2004/0246440 | A1* | 12/2004 | Andino et al. .......... 351/177 |

OTHER PUBLICATIONS

Fernandez et al., "Robotic Manipulation of Ophthalmic Lenses Assisted by a Dedicated Vision System", May 1998, IEEE.*

Phillips, "Continous Evolution: Today's Soft Contanct Lenses", 2001, Coopervision.*

PCT International Search Report, dated Oct. 27, 2003, for PCT Int'l. Appln. No. PCT/US03/11136.

CNC Machining: Main Page, *Department of Mechanical Engineering, University of Pennsylvania*, Jan. 21, 2004, http://www.seas.upenn.edu/~meam100/cnc/cnc_main.html, 2 pages.

* cited by examiner

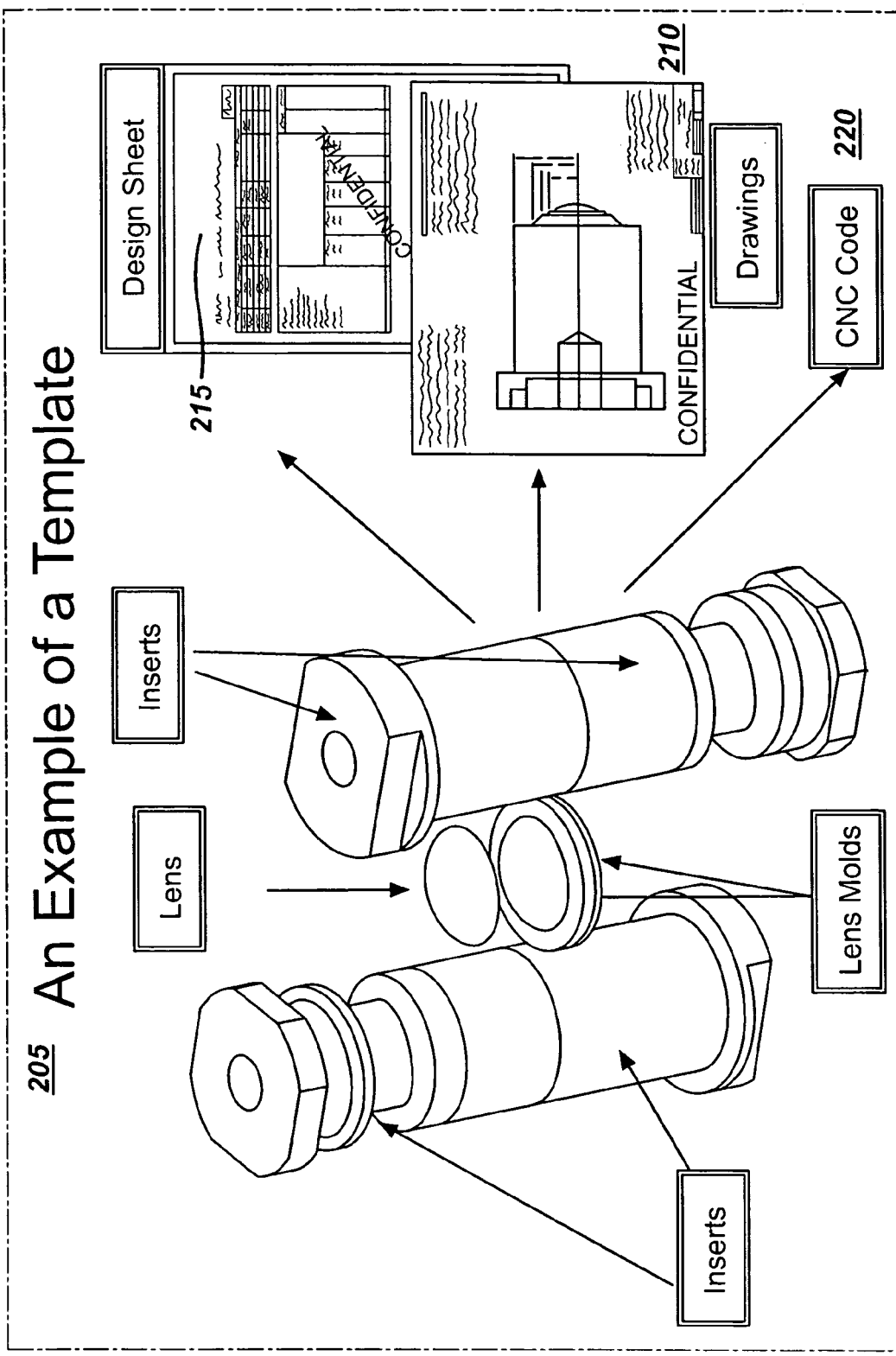

FIG. 6(b)
Output:
Lens Mold Designs
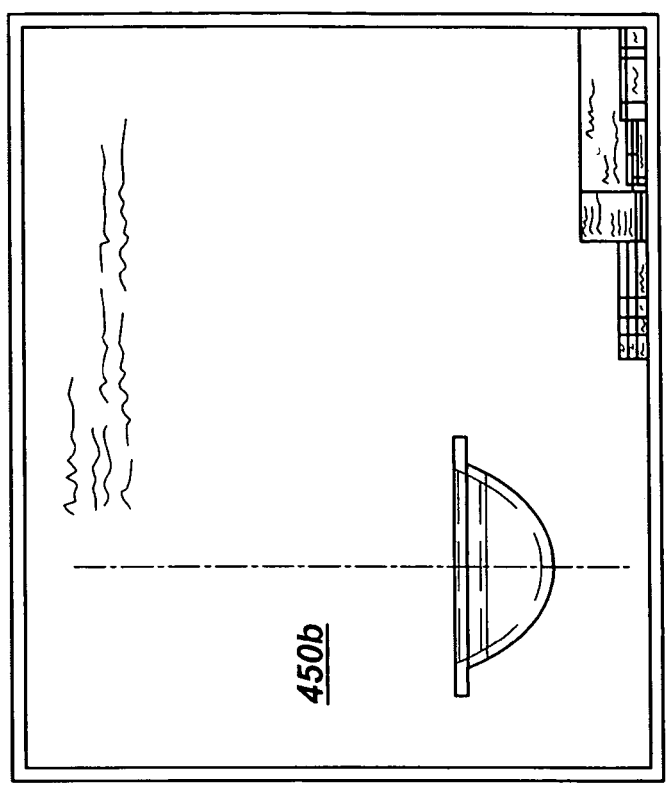
450a
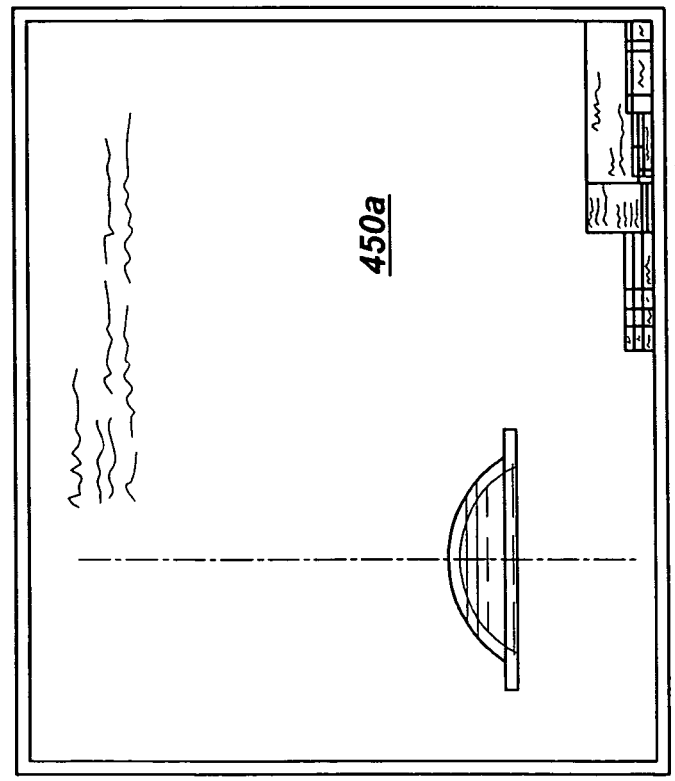
450b

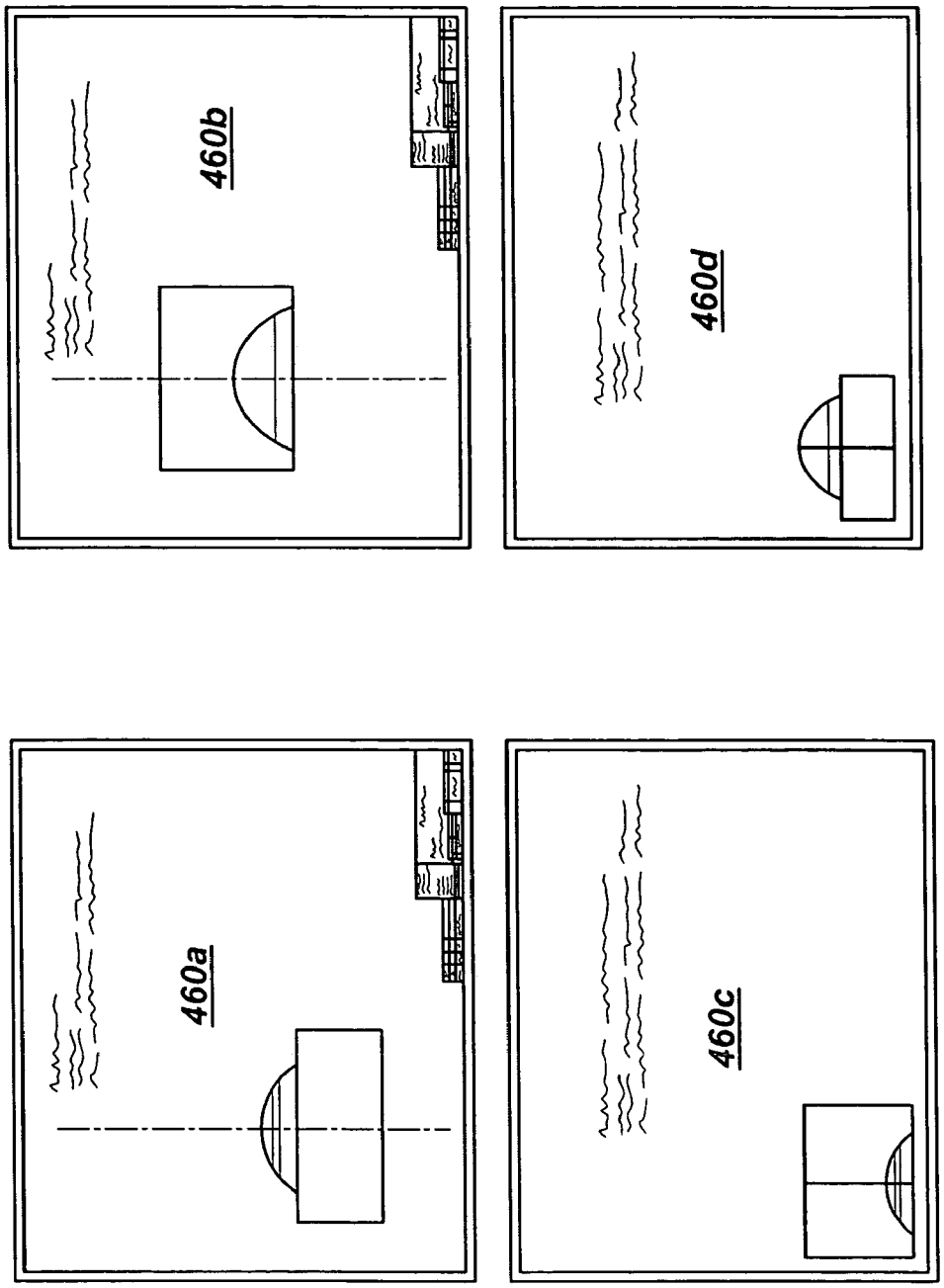

DESIGN BUILD TEST CYCLE REDUCTION

This is a non-provisional application that claims priority from U.S. Provisional application Ser. No. 60/372,738 filed Apr. 12, 2002

FIELD OF THE INVENTION

The invention relates generally to contact lens, lens mold & insert design and manufacturing arts, and particularly a design methodology and tool for reducing the Design-Build-Test Cycle Times of new and existing ophthalmic lens products, including mold inserts and mold items implemented in contact lens design and manufacturing processes.

DISCUSSION OF THE PRIOR ART

Prior to manufacturing a contact lens, a design concept must be generated and parameter/process verification must be established. In practice,a research and Development Group is responsible for developing and producing lens design concepts, and proving the manufacturability of them through prototype manufacture, clinical trials and scale-up activities.

A Product Development Group consisting of (mainly) Lens Design, Plastic Processing and the Tooling Development Groups within a research and development entity is responsible for ensuring that the lens design is producible before releasing it to Operations. Once the scale-up activities are complete, the relevant information is generated for the Operations Group for full-scale production in order to generate salable product.

A breakdown of one such process 10 is described with respect to FIG. 1. Typically, as represented in a first step 12, the Lens Design Group in most contact lens manufacturing companies creates conceptual lens geometries using a combination of a custom developed software and 2D graphing tools (e.g. Visual Basic Applications and AutoCAD)—referred to herein as the "custom developed design software". Usually, this group also generates the lens mold designs, the insert designs and the core designs 16 that are used in the lens making process. The custom developed design software is implemented to generate initial new designs, as indicated at step 15, by using estimates of the processing conditions being used on the pilot lines (i.e., lens making equipment). The mathematical relationships that exist between the actual manufactured lens molds and the actual produced lenses are referred to as "hydration factors". The relationships linking the actual manufactured inserts to the produced lens molds are referred to as "shrinkage factors". Typically, throughout the contact lens industry, it is known that there are three main directional factors used for each of these expansion and shrinkage factors—radial, sagittal and diametral. It is often easier to mathematically model just four (4) of these factors (two for shrinkage and two for hydration) without significant loss of accuracy. This is achieved by setting the diametral and sagittal values equal to each other that reduces the complexity of relating the lens to the molds and inserts substantially. This, however may not model 100% accurately what is actually happening in the physical process of making contact lenses.

Usually, all of the data 20 relating the manufactured lens to the initial lens design, lens mold designs and insert designs is held within the Lens Design Group 15 and used in the custom developed design software. Once the Lens Design Group has completed a lens design, the relevant insert and core designs are passed from them to the Tooling Development Group where the complex mold and insert geometries are machined, as illustrated in steps 22 and 25. The respective insert may be built, for example, utilizing Single Point Diamond Turning technique. The Tooling Development Group particularly manipulates the custom developed design software printed output, text files or AutoCAD files (for example) to generate into CNC (computer numeric control) data. This tool path data directs the lathe on how to produce the desired part profiles.

Once the inserts have been machined at step 22, they are passed (along with the lens mold designs and targets from the Lens Design Group generated at step 15) on to the Plastic Processing Group, where they are used to injection mold the lens molds as indicated at step 25. Before these lens molds can go on to produce contact lenses, metrology data (including radius and sagittal measurements) are taken to determine whether the lens mold targets (as specified by the Lens Design Group) are met. When this is not the case, the injection molding conditions may be modified to change the lens mold geometries, until the lens mold targets are be met. This lens feedback condition is depicted as a loop 26. Typically, if the targets cannot be met, the process returns to step 15 to once again involve the Lens Design Group to issue new data, and initiate the build of new inserts. These feedback steps are represented as steps 27. Once the lens mold targets have been met in the injection molding process at step 25, more lens molds are fabricated and passed down to the contact lens making process at step 30.

Metrology data is taken from the manufactured contact lenses (including diameter, base curve radius, center thickness and power) and is passed back to the Lens Design Group (with the lens mold metrology) for analysis as indicated by feedback loop 31. This analysis yields new figures for shrinkage and expansion, as produced by operating the Pilot Line and may result in a contact lens manufactured not according to design specifications. This being the case, the custom developed design software and the Lens Design Group 15 are involved in the loop again, relating the initial intended lens design to the newly calculated shrinkage and expansion data to give new lens mold and insert designs 16. They can either do this by modifying the process parameters they used for the previous iteration, modify their source code of the custom developed design software, or modify the lens design, before re-issuing the lens, mold, insert and core design data 16 again for the next iteration.

As depicted in FIG. 1, the insert, lens mold and contact lens manufacture process then starts again, although this time, the produced lens should be closer to target than the first run through. Often times, because there are at least four lens parameters that have to be met (base curve, diameter, center thickness and power), one parameter at a time is attempted to be corrected, thus having at least four iterations 31.

From the process described so far, it is common that that all iterations have to go back to the Lens Design Group at step 15 because the custom developed design software "links" relating the lens to the molds and the molds to the inserts and cores, for regulatory control reasons, is generally not available to anyone outside this group. The custom developed design software can be very complex and evolve over many years. As the software evolves to capture more and more different lens designs, the code writers edit and add to their source code.

Once the correct contact lens has been manufactured to meet the original lens design intent, and the process and product parameters are within specification, the process is repeated for different skus (stock keeping units) so as to generate a calibration curve. This can take up to six iterations (not shown). Once the calibration curves are known, a "design packet" is transferred to an Operations Group, where the final salable product is manufactured.

It should be understood that, in view of FIG. 1, at step 33, after clinical trials for the lens products are conducted, the Design Build Test (DBT) process may even require looping back to the conceptual or lens design stages in order to correct or modify the lens design. For example if the lens does not perform as well as was expected, further lens design modifications may be made to further optimize the design.

The above system is a very time consuming exercise, and can take up to eight months and up to six iterations to develop and prove a new contact lens design and have the product available to the consumer. Additionally, the Lens Design Group can be very heavily involved, when they don't necessarily need to be as most of the changes between iterations are new values for the shrinkage and expansion relationships (process parameters). The Lens Design Group thus, should be focusing on new innovative designs independent of process, and not functioning to fit the process to the intended product.

Due to its complexity and evolution, the prior art custom developed design software availability is limited to just a few people.

As there are currently no commercially available, off the shelf software packages that are used for designing contact lenses, and/or lens molds and/or inserts, moreover, that related these to the various complex manufacturing processes via machine code ("CNC"code), many contact lens manufacturers write their own code (computer Furthermore, the manufacturing processes used in contact lens/lens mold/insert manufacture can be extremely complex and hence writing mathematical algorithms for process simulation is very difficult, if not impossible.

There is thus a need for better modeling of contact lens designs, their related lens molds, inserts and core designs, and modeling of the manufacturing process so that the entire process from initial concept through to the calibration curve optimization time, hereinafter referred to as the Design-Build-Test Cycle Time, can be greatly reduced.

Moreover, a need exists for a system and method that enables the design of ophthalmic contact lenses, and/or contact lens molds and/or inserts, and relates associated lens/lens mold design data to various complex manufacturing processes via machine code.

In the contact lens design, development and production stages, the material for the lens is developed, the lens geometry calculated, the plastic lens mold part drawings are designed, and the mold tools built. Once the tools are complete, the plastic lens molds and the lens are made. At this stage, the final product is examined to assess whether the design has been achieved. Changes to the designs often take place by modifying particular lens zones to solve particular problems, e.g. power, center thickness, base curve or diameter, etc. The use of individual computers for specific use is not bad, but the use of separate databases is not good because there is no integration of data. That is, another time consuming exercise is to obtain accurate and up-to-date process parameters since there exist many different non-integrated databases. The current individual databases closely resemble a hierarchical database, which is very rigid. The data that is used pertains to the plastic shrinkage characteristics, lens monomer expansion factors, lens geometry characteristics and mold tooling expansions.

Thus, there is a further need for the generation of a database for storing all product and process parameters pertaining to the contact lens designs, their related lens molds, inserts and core designs, and modeling of the manufacturing process, so that the Design-Build-Test Cycle Time may be reduced.

SUMMARY OF THE INVENTION

It is thus an object of the present invention to provide a more robust ophthalmic lens design and modeling tool that facilitates rapid design and build and test (DBT) manufacturing phases.

It is a further object of the present invention to provide a more robust ophthalmic lens design, lens mold design and insert design modeling tool that generates for users 3-dimensional views of lens designs and provisions for manufacturing information capable of being imported to a lens manufacturing facility for rapid development of lenses in order to reduce DBT cycles.

It is another object of the present invention to provide a three-dimensional modeling tool for designing ophthalmic lenses that enables the contact lens physical dimensions and design to reach their target specifications as soon as possible, resulting in reduced Design-Build-Test Cycle Times. Reduction of the Design-Build-Test Cycle Times of new and improved contact lens designs using commercially available 3D modeling software packages (such as I-DEAS® or any other 3D modeling software product—hereafter referred to as "3D CAD/CAM modeling software"), hence increases speed to market of new lens designs.

According to the principles of the invention, there is provided a system and method capable of importing a lens design in either text, or CAD file data type, or any other common way of electronically representing design information or that a lens can be designed within 3D modeling software. Using a template-based approach, the system generates lens and/or mold and/or insert designs and ultimately cause issuance of the relevant part manufacturing code (e.g., CNC code) through the use of the 3D software.

For the design of new lenses or modification of existing lens designs, the 3D CAD/CAM modeling software first requires importation of the lens design data via text files or CAD files or any other electronic media format. The lens design data is "template based" such that the lens design is re-generated, and then the lens mold design and insert designs created from the lens model are made available to a manufacturing plant as template outputs. This process also allows for contact lenses and/or lens molds and/or mold inserts to be designed directly inside the 3D modeling software, and is not restricted to using the template-based functionality. That is, stand-alone parts may additionally be designed within the 3D CAD/CAM modeling software tool.

If any process parameters, lens design or any other component need to be changed, these are readily accomplished through changing the relevant feature in the template. The template automatically updates any other features that are affected by the imparted change(s). Once a satisfactory lens/lens mold/insert design is achieved, machining data and engineering drawings are issued from the templates and sent to a Tooling Group for suitable manufacture.

The templates and associated 3D models may be stored in a database for subsequent access. Once a template is built in the 3D software tool, the fully associated 3D models may be accessed, in addition to the functionality for creating new or modify existing lens designs.

Advantageously, use of Non-Uniform Rational B-Spline (NURB) based 3D modeling software such as provided by the "3D CAD/CAM modeling software" tool alleviates the need for individuals to write lines of computer code for the lens, lens mold and insert designs, and also provides more flexibility to model the process more accurately—for example by applying spline curves, polynomials etc that are already pre-defined in the software. Simulation of the manufacturing process is also possible, using tools like "mold, flow, cool and warp" analysis software on 3D models.

The traditional approach of "custom-written software" is usually only accessible and fully understood by the "author(s)" and usually involves writing mathematical equations to define geometry, and hence the product being designed. The more complex the product, the more difficult and time consuming is the exercise to design the required product. By contrast, one does not need to be an expert in 3D modeling to use these modern 3D tools, which usually involve using pre-existing geometry features to generate fully constrained complex surfaces (mathematical equations can be obtained by interrogating the geometry if so desired). Only minimal mathematical equations are required to link the contact lens to the lens mold and then to the insert.

The 3D modeling system according to the invention further includes built-in revision controls that are 100% accurate, and the data can be shared readily amongst many different types of customers. The ability to view the 3D models and the 100% accuracy of the solid models minimizes the errors that can be present in such complex software systems. This also helps to quickly find any flaws in the system, and allows modifications to be made very quickly. The data output and export options of 3D systems can link directly to many other commercially available software programs, including web browsers.

Some other advantages of using the NURB based 3D modeling software such as provided by the 3D CAD/CAM modeling software tool includes: automatic volume calculation; automatic center of gravity calculations; automatic interference checking; powerful export capabilities; no need for complex mathematical equation solving; no need for manual line-by-line computer programming; the ability to "point and click" when designing products.

BRIEF DESCRIPTION OF THE DRAWINGS

Details of the invention disclosed herein shall be described below, with the aid of the figures listed below, in which:

FIG. 5 depicts a template 200 providing some example components and user interfaces required for designing, creating, and modeling lens, lens mold, and insert components within the 3D modeling platform of the invention; and, FIGS. 6(a)–6(c) depict exemplary lens, lens mold design and insert design data sheets that are used in production and generated by the 3D modeling software.

DETAILED DESCRIPTION OF THE PREFERRED EMBODIMENT

Figure 1:
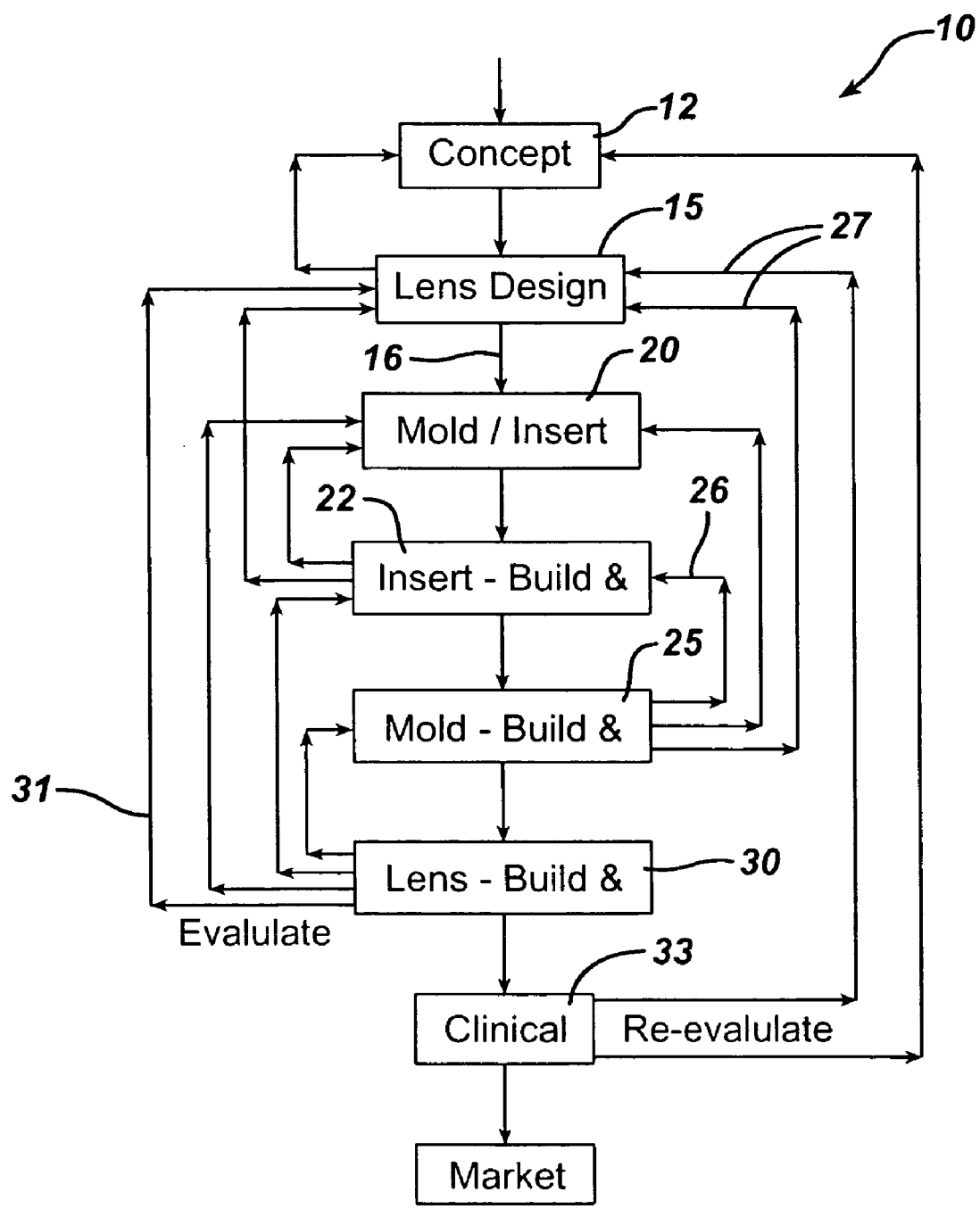
FIG. 1 is a process diagram illustrating the Design Build Test Cycle according to the prior art.
Figure 2:
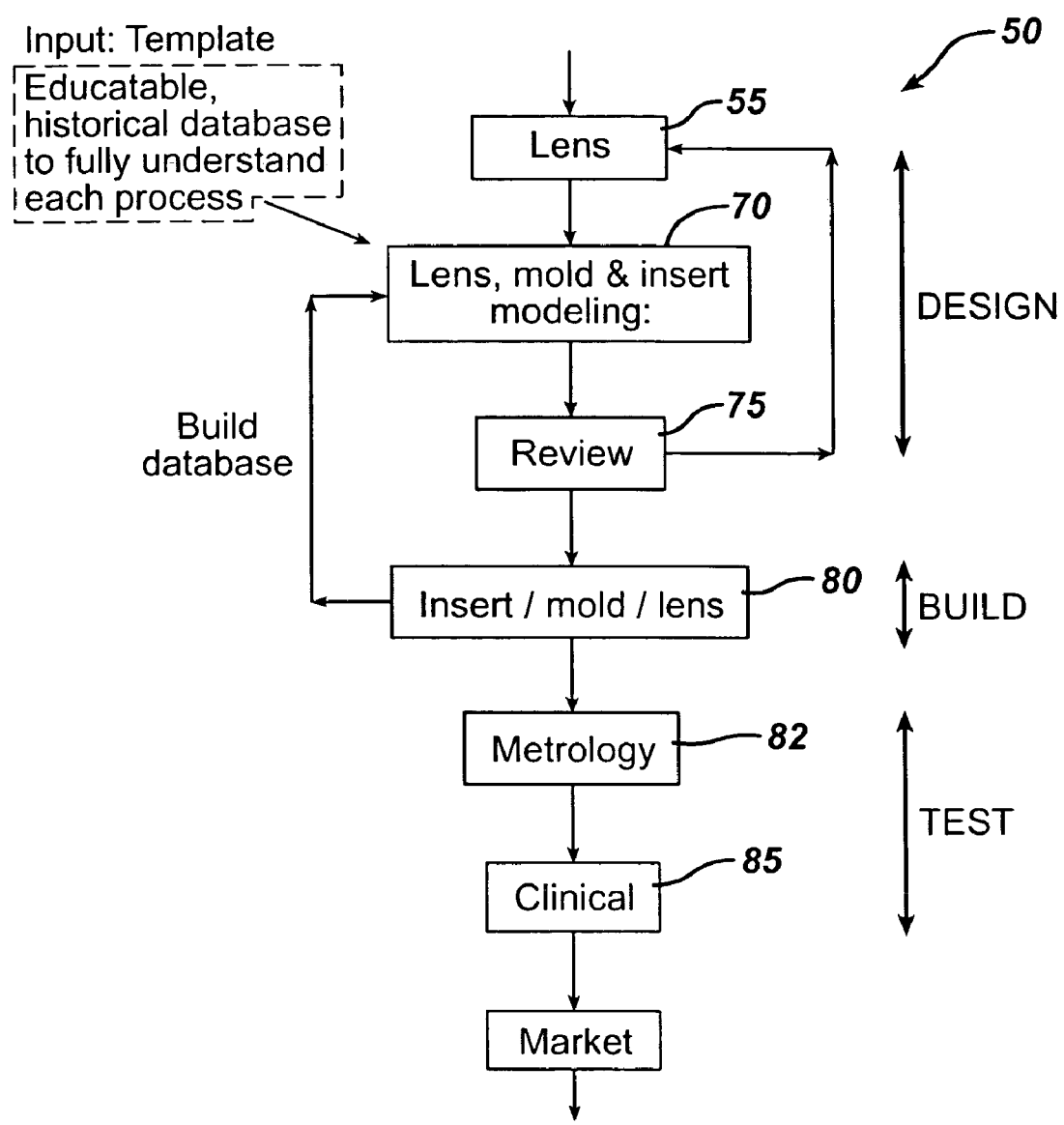
FIG. 2 is a process diagram illustrating the Design Build Test Cycle according to the present invention.

The robust ophthalmic lens design and modeling system providing efficiencies for rapid design and build and test (DBT) manufacturing phases according to the invention is illustrated in FIG. 2. As shown in FIG. 2, the design and build and test (DBT) manufacturing phases is substantially streamlined than the prior art system of FIG. 1 due to the benefits of the modeling system efficiencies. Particularly, after a lens design step 55, there is performed a lens model generating step 70 for the generation of a lens modeling template associated with that design and which comprises all the manufacturing data required for its manufacture within specifications. Preferably, the template specifies data including: lens design parameters (e.g., power, diameter, base curve and center thickness, cylinder, various radii and zones, etc.), FC and BC core surface specifications, and manufacturing process parameters (such as shrinkage of plastic from the insert, for example, and/or hydration of the contact lens monomer (from the lens mold), for example, which values change based upon how the Pilot Lines and/or Manufacturing Lines are operating. A key input of this modeling step is the generation of assembly equations which link these process parameters to the physical parts, e.g., lens to lens mold, lens mold to mold inserts, for example. The template build, lens modeling and database build steps 70 will be described in greater detail herein with respect to FIG. 3.

In FIG. 2, after lens design and 3D modeling steps there is performed a review step 75 wherein the actual lens models are evaluated. That is, at this stage, the final product is examined to assess whether the 3D design has been achieved and to perform interference checking or detect obvious errors in the model. If necessary, another iteration through lens design may be necessary to tweak the lens/mold/insert design and/or manufacturing parameters in order to achieve the lens design. These are input through the template user interface. For instance, if the Lens Manufacturing Lines are operating at a particular condition affecting expansion/shrinkage, these process parameters and the assembly equations may be accordingly modified. Once it passes review, the actual mold inserts and lens molds are constructed from the 3D modeling templates and output template information as indicated at step 80. According to the invention, the 3D template based approach means that all parts are mathematically linked to each other, and constrained geometrically thus, eliminating errors that may result from programs implementing 2D coordinates. The elimination of errors reduces the Design Build Test cycle. The generated templates, and associated lens design, modeling and manufacturing information are stored in a database 60. That is, the database 60 stores all data generated through templates so that the all of the data (manufacturing coded, CNCs, drawing) are saved and accessed by user over a network, for example. New templates can either be created from scratch or from similar templates that can be modified in order to generate new lenses and/or lens molds and/or mold insert products.

With further respect to FIG. 2, thus, after insert/mold/lens build stages, metrology 82 and clinical evaluations steps 85 are performed. However, as the generated 3D modeling templates comprise all information sufficient for achieving a manufactured lens design with rapid convergence within lens design specifications/tolerances, then, contrary to the prior art, the need for re-evaluation by a Lens Design Group at these steps is unnecessary. That is, the Lens Design Group only needs to be involved if the lens design needs to be changed.

The present invention particularly includes the implementation of a 3D solid modeling technique implemented in Non-Uniform Rational B-Spline (NURB)-based modeling and visualization systems. By utilizing 3D solid modeling software it is now possible to capture the lens, lens mold and insert design intent, retaining the 100% accurate relationships between any of the parts. Everything is based on geometry, and so when one feature changes on one part, e.g., insert, lens mold or lens, the other components that are dependent on it also change automatically as they are all related to each other by assembly equations. Other 3D modeling software may now be capable of performing similar functions including products from Unigraphics and, Pro Engineer (from Parametric Technology Corporation). Such software has been utilized to easily accommodate complex relationships between parts, including all three (3) industry standard and accepted shrinkage and expansion factors (diametral, sagittal and radial) without the need for a programmer to write complex links between them. With 3D modeling, users are not restricted to just spherical geometries; that is, aspheres may be just as easily modeled and used as driving parameters, as can any conic section or polynomial or spline function. Non-rotationally symmetric and arbitrary surface geometries are additionally treated in this manner with 3D CAD/CAM modeling software. In short, the NURB-based software has vastly superior flexibility to allow any geometry to be modeled and constrained for use, without having non-programmers writing code.

According to the invention, the template based lens modeling approach is utilized for the lens designs which include, but are not limited to: spherical lenses; bifocal lenses; multifocal lenses; toric lenses (with and without stabilization zones); toric multifocal lenses (with and without stabilization zones); non-geometrically defined lenses (e.g., point cloud surfaces) and zemike surfaces to describe the surfaces.

Figure 3:
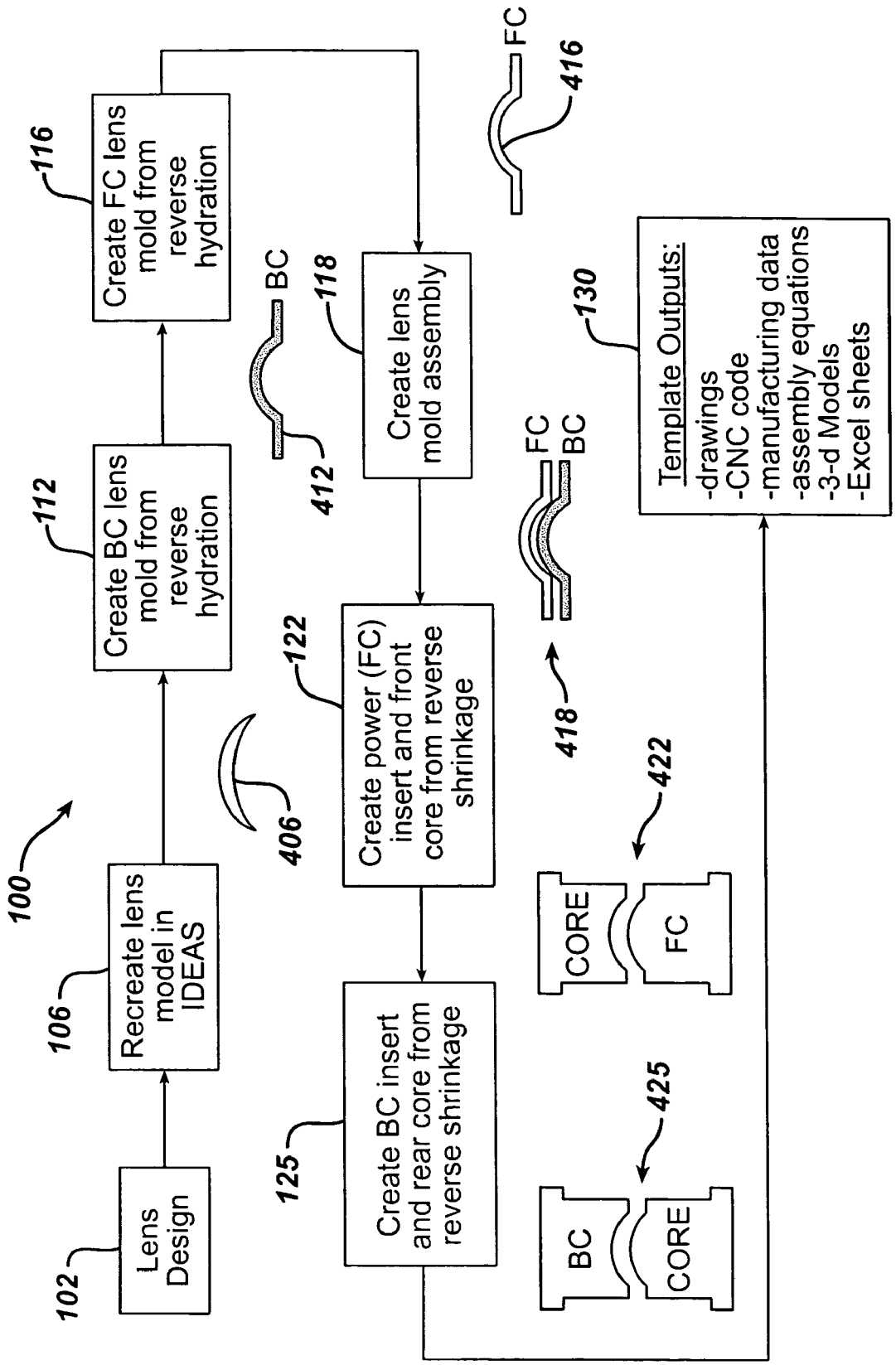
FIG. 3 illustrates the template build process 100 using the 3D modeling tool and with one of the inputs being the lens design, according to the present invention.

Referring back to step 70 of FIG. 2, there is now described in greater detail, the process for building the lens, mold and insert component design and manufacturing templates. FIG. 3 illustrates the process steps 100 for modeling these components within, for example, the I-DEAS® software tool (or similar 3D CAD/CAM modeling software) particularly, the template build process according to the present invention. It is from the program flow /structure of FIG. 3 that describes how the program files (e.g., macros) behind the templates relate to each other and how these macros are used to extract the dimensions from the parts and convert the data into outputs, as indicated at step 130, including, but not limited to: three dimensional (3D) lens/lens mold/mold insert models, CNC code, excel spreadsheets comprising manufacture information, and, drawings including 2-D drawing outputs related to the selected lens design and used in the lens manufacture.

In FIG. 3, a lens design created by a Lens Design Group, is first imported into the I-DEAS® software tool (or similar 3D CAD/CAM modeling) software, as indicated at step 102. The system developed is capable of importing a lens design in either text, or CAD file data type, or any other common way of electronically representing design information. It should be understood that, rather than inputting the lens design information, alternately, the lens may be designed within the 3D CAD/CAM modeling software, and used as a direct driving model for the lens molds and inserts. The relationship between the lens and lens molds (inverse expansion) may be modified in the software as described with respect to FIGS. 4(*a*) and 4(*b*), as may the inverse shrinkage linking the lens molds to the inserts. It should be understood that these methods are compatible with the template-based approach. After the lens design step and related input of the template drive file at step 102, the template build steps 106–130 are performed.

In order to create a new template, the individual parts (lens, lens molds, inserts and cores) are preferably designed first. Rotationally symmetric designs entail the sketching and revolving of each part's cross-section, for example, using point-and-click functionality. Non-rotationally symmetric parts require additional features beyond the initial cross-section revolve. Each part has all its critical dimensions labeled according to a nomenclature scheme. Part naming also follows an agreed upon naming convention. This allows for the correct assembly equations to be laid out. While parts are being dimensioned, careful attention to detail and analysis as to which dimensions will be used as driving parameters vs. which dimensions will be driven (reference) parameters. Driving dimensions are dimensions that can be directly modified by the user, or through the use of macros, and are responsible for driving (changing) similar dimensions on the other parts (lens, lens molds or inserts). Reference dimensions are dimensions that cannot be modified directly, but result from other dimensions that fully constrain the model. For example, to fully constrain an arc, the "radius", "x center", "z center" and "x end" could be driving dimensions but the "z end" value would be a reference dimension. The nature of the modeled geometry dictates that only a few dimensions are required to fully describe (constrain) the part. However, additional reference dimensions are added for use in assembly equations as well as CAD drawings. The template build steps include: an initial step of 106 of recreating the lens model in the I-DEAS® software tool (or other 3D CAD/CAM modeling software), as depicted by a corresponding lens model 406 in FIG. 3; a step 112 of creating a back curve (BC) lens mold from reverse hydration as depicted by a corresponding BC model 412; a step 116 of creating a front curve (FC) lens mold from reverse hydration as depicted by a corresponding FC model 416; and, a step 118 of creating a resultant lens mold assembly, as depicted by a corresponding lens mold assembly model 418, including generation/modification of the related linking assembly equations. The tool designer then designs the cores based on the critical surface geometries, lens mold design intended thicknesses and material chosen—although this may be an automated process. Particularly, the core geometries drive the non-critical sides of the lens mold design and the assembly equations preferably drive all 'loose' dimensions on all the parts, capturing all possible degrees of freedom. Thus, as shown in FIG. 3 step 122 involves creating a power (FC) insert and front core giving shape, dimension and volume to the FC lens mold including generation of related linking assembly equations for reverse shrinkage. A corresponding FC core/FC insert model 422 is depicted in FIG. 3; a step 125 of creating a BC insert and rear core giving shape, dimension and volume to the BC lens mold and generating related linking assembly equations for reverse shrinkage. A corresponding BC core/BC insert model 425 is depicted in FIG. 3. It should be understood that, throughout the process steps 106–125, point-and-click functionality is enabled by the 3D modeling tool permitting lens designers to easily modify lens surfaces by pointing, clicking and dragging lens surfaces via the interface. This may additionally be achieved by the user entering commands at a prompt, and/or by user-defined macros. By modifying the lens geometry, or the process parameters used in manufacturing, in the manner as will be explained, all the relevant parts are updated quickly and accurately. Finally, at step 130, in FIG. 3, the generated outputs are made available to the tool room for enabling the component manufacture. That is, for a Tooling Development Group, the 3D models of the inserts and cores may be directly used to generate engineering drawings and the CNC tool path data required by the lathes, thus, obviating the need to re-draw the parts in AutoCAD or similar, and saving much time.

With more particularity, the 3D CAD/CAM modeling software allows for the generation and display of a user interface which provides functionality for retrieving existing lens model templates from the memory storage system, e.g., database 60 as depicted in FIG. 2, and functionality for editing and generating new lens model templates. Exemplary illustrations of a template build user interface depicted in FIGS. 4(a) and 4(b).

Figure 4A:
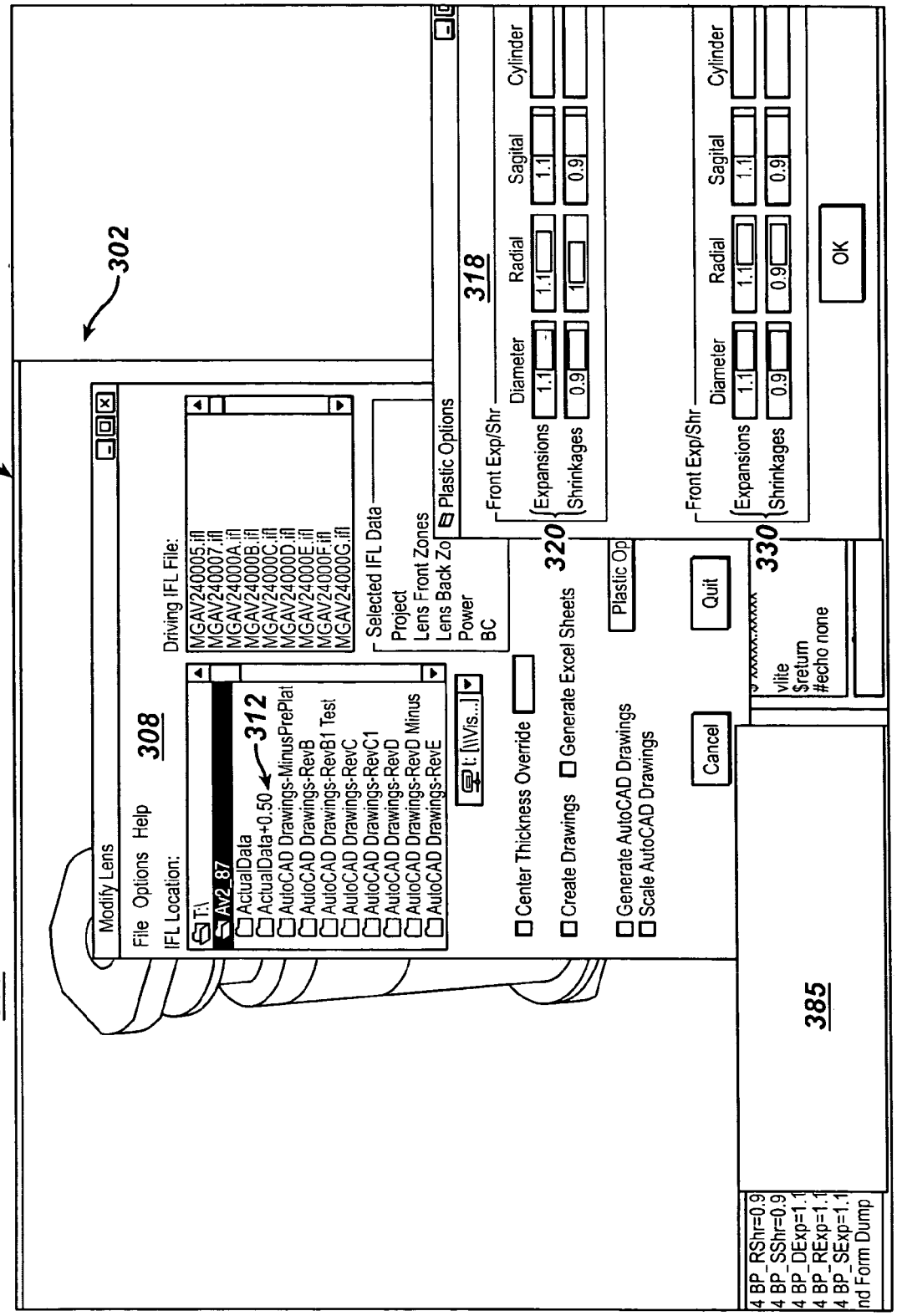
FIGS. 4(a) and 4(b) illustrate example user interfaces providing functionality for specifying and modifying the relationship between the lens and lens molds assembly (inverse expansion) and, mold inserts, as may be performed via 3D modeling software according to the invention.

FIG. 4(a) is an exemplary user interface 300 (created by using I-DEAS®), which includes a display area 302 for displaying various informational and graphical lens design and lens manufacturing models, including 3-dimensional lens design models. Other 3D CAD/CAM modeling software also has the capability for building similar interfaces to the one created in I-DEAS®. As shown in FIG. 4(a), via a generated window 308, a user may access a variety of files 312, each comprising lens design data, that may be stored, for example, in the memory storage and/or database system. It is information from these files that drive the template. That is, after lens design is pulled in with a text file, then a further screen is generated such as the exemplary "plastics options" window 318 illustrated in FIG. 4(a). From this window display 318, a user may specify respective front curve and back curve expansion and shrinkage parameters, e.g., via entry fields 320, 330. It is these values that are applied to the selected lens design 312 and become useful for lens mold design and, additionally provide data from which mold inserts are generated.

As described, after creating all the parts to be used in the template (lens, lens molds, inserts and cores, an "assembly" is created (step 118, FIG. 3) which comprises generation of assembly equations included for the lens design template. In one scheme, the lens design and the process parameters (namely shrinkage and expansion factors), define the critical geometry sides of the lens molds and inserts. The assembly equations are put together such that the lens geometry is scaled down (by the inverse of the expansion) to drive the lens mold geometry on its critical side. The lens molds, in turn, drive the insert geometry (scaled by the inverse of the shrinkage value).

Figure 4B:
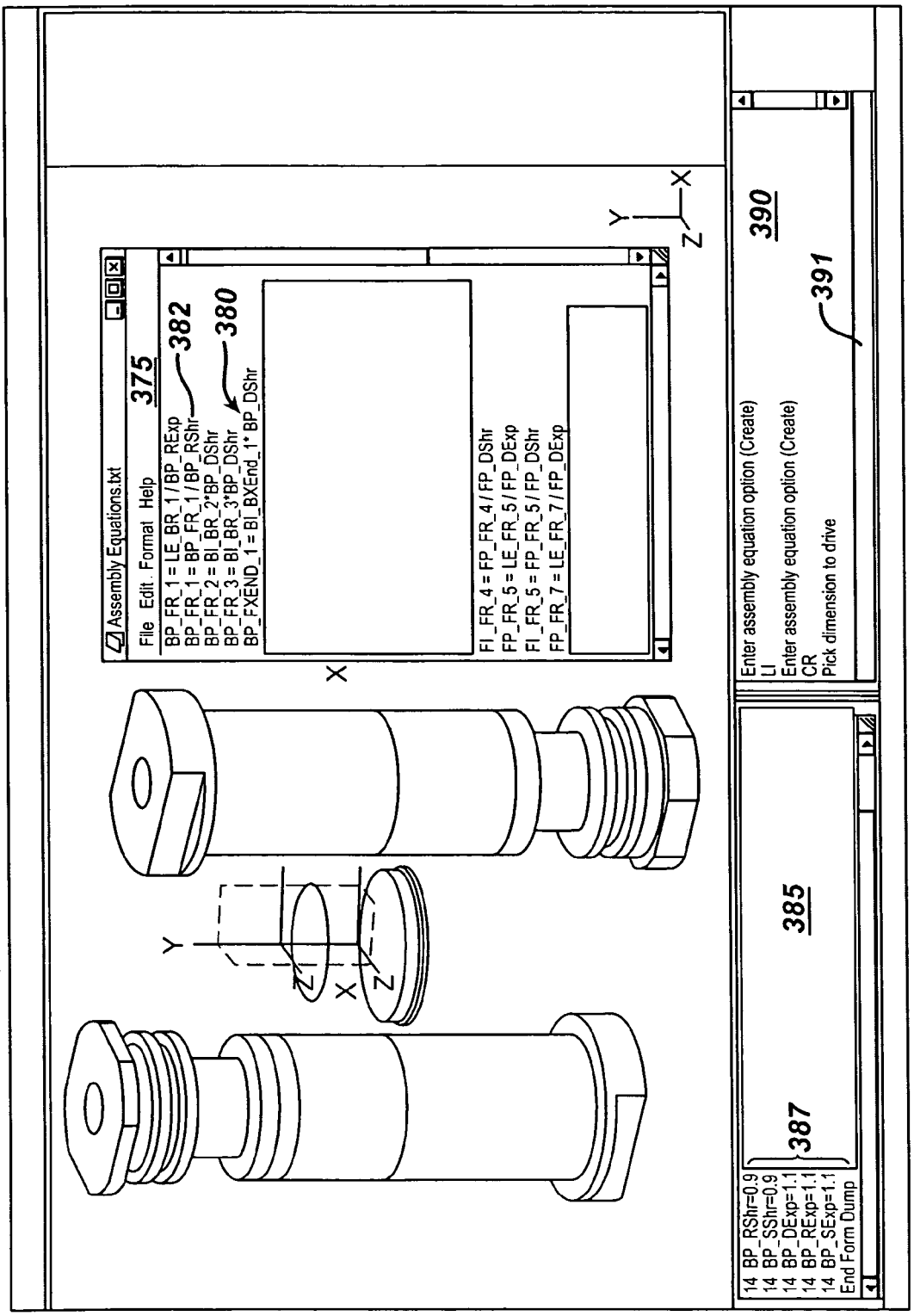

FIG. 4(b) particularly illustrates an assembly equation interface screen 350 detailing the list of assembly equations 375 associated with the design and manufacture of a lens. Particularly, a file, e.g., "Assembly Equations.txt" file associated with a selected (or new) lens design, is retrieved from the database and comprises a list of assembly equations 380 that link the lens to the lens mold, and the lens mold to the inserts of that lens design. For instance as shown in FIG. 4(b), an example assembly equation 382 governing the link between the lens mold and the lens is specified as:

$$BP\_FR\_1 = LE\_BR\_1/BP\_RShr$$

which relates the back plastic front radius with the back radius for the lens divided by a back plastic radial shrinkage parameter value, for example. As presented via interface 350, a window 385 provides a scrollable list of the radial shrinkage (e.g., BP_RShr) and radial expansion (e.g., BP_Rexp) factors 387 based upon the lens current Manufacturing Line. These may be utilized as inputs to the assembly equations 380 that link the lens manufacturing processes to the lens design (step 102). Thus, depending upon factors such as the type of materials, process conditions, these equations will change. The interface 350 additionally provides a window 390 including an entry field 391 for enabling entry of new assembly equations and enabling entry of particular dimension the assembly equations drive. As shown in the assembly equation build interface screen 350, assembly equations 380 may be imported or created within the I-DEAS® software tool, as shown. Other 3D CAD/CAM modeling software also has the capability for building similar interfaces to the one shown here in I-DEAS®

Returning to FIG. 3, according to the template build software running in the 3D CAD/CAM modeling software, equations utilizing process parameters that govern lens Manufacturing Lines operating conditions are provided for: linking the lens design (step 106) with the manufacture of a BC lens mold (step 112); linking the lens design (step 106) with the manufacture of a FC lens mold (step 116); and, linking the manufacture of a BC lens mold and an FC lens mold (step 112) with a resultant physical lens mold assembly (step 118). The lens mold assembly equations (step 118) are further linked with the FC power insert design, the BC insert design and the respective core designs (step 122), for example. The specification of the current process parameters is specified in the plastics option screen 318 of FIG. 4(a). It is from these interfaces that enables a user to modify, generate and store lens design/build templates.

Figure 6A:
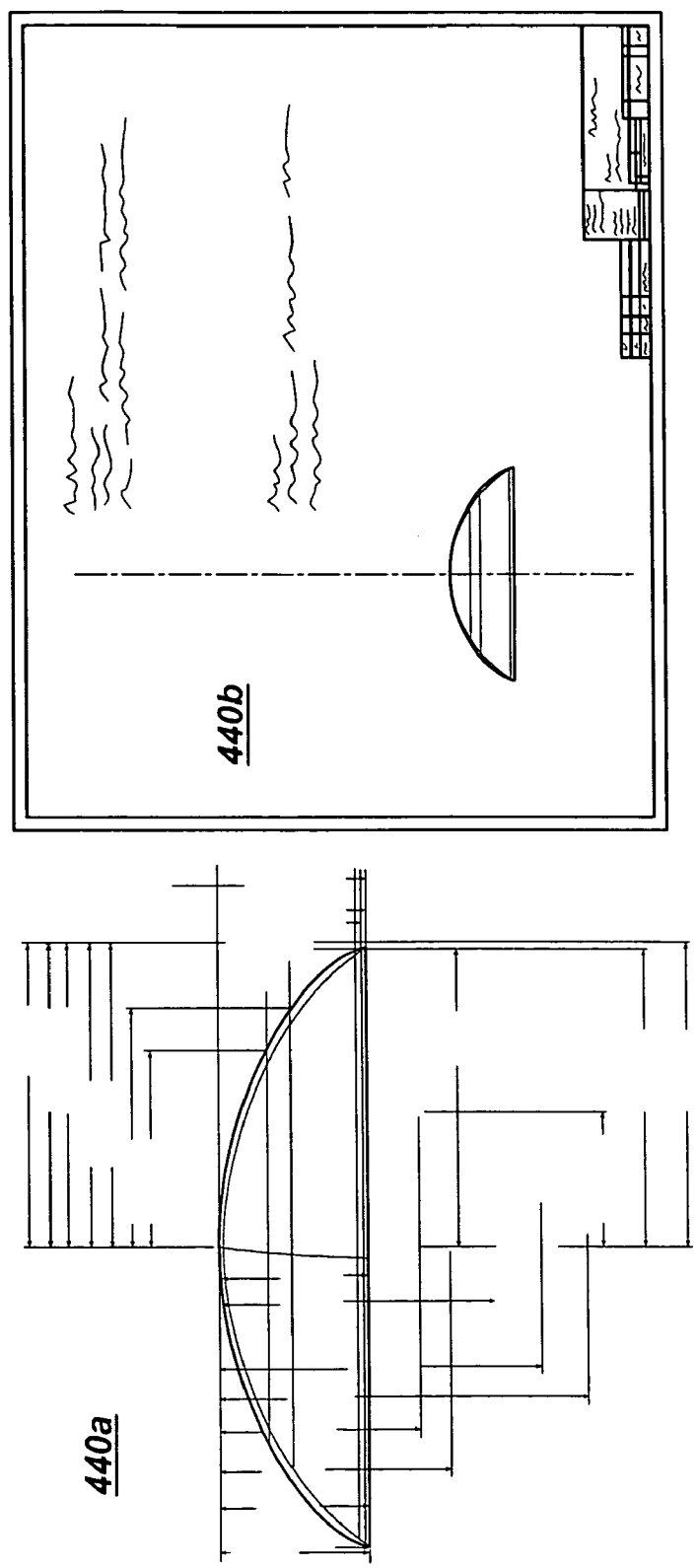

The culmination of steps 106–125 in FIG. 3 results in the generation of a template 200 such as shown in FIG. 5. That is, as shown in FIG. 5, the templates 200 provide a user with product design information in a variety of formats, including: 3-D models 205 of the lens and/or mold and/or insert designs, 2-D design drawings/graphics 210, design sheets such as spreadsheets 215, etc. and, the generation of and issuance of the relevant part manufacturing (computer numeric control) CNC code 220 through the use of the 3D software. The quick and reliable presentation of lens design and manufacturing information afforded by the 3D CAD/CAM modeling software provides users with a greater understanding of current lens products. The system further permits users to modify existing templates for generating new lens designs if applicable, which also reduces the DBT cycle. Exemplary lens, lens mold design and insert design data sheets that are used in production and generated by the 3D CAD/CAM modeling software are shown in FIGS. 6(a)–6(c) and include 2D engineering drawings 440a, 440b of lens designs created, for example, within the I-DEAS® software tool (FIG. 6(a)), 2D engineering drawings 450a, 450b of lens mold designs (FIG. 6(b)); and, 2D engineering drawings 460a–460d of mold insert designs created, for example, within the I-DEAS® software tool (FIG. 6(c)). In a more advanced modality, the software applications not only update the lens, but also create the following deliverables, (including but not limited to): individual part drawings with a tabular list of dimension values; design sheets in Microsoft® Excel format (for example) for the parts; and other machine code (e.g., M&G Code, text files, etc.) that are utilized in the manufacturing of the inserts or lens molds or lenses.

Returning to FIG. 5, once the template 200 has been designed and verified, a program file can then be called, which in turn calls other software applications (example program files are "DimDump" (opens Excel returns the dimensions of all driving dimensions (and reference dimensions) of the part being queried) and "ModDims" (creates via the user interface the ability to modify dimensions by the user)—both these can open Excel as the data dumping/reading media) to view dumping data and create the design sheets. These software applications allow the user to select a lens design file and relevant process parameters as input for the template. In a basic modality, these software applications read the lens design file, verify it against the lens part in the template (to ensure compatibility and data integrity, etc.), and update all the non-referenced values with the appropriate values from the lens design file. The assembly is then updated and the assembly equations update the values of all the affected parts. The result is a template with the lens design recreated in 3D format, and the corresponding lens mold designs and insert designs necessary to make such lens, with graphical and numerical output (e.g., CNC code) to enable the manufacture of the relevant components.

An exemplary process for automatically generating M&G code (or CNC code) for tool path generation as implemented by the system is now described with respect to FIG. 7. As shown in FIG. 7, a high-level process flow 500 is described that depicts steps for automatically generating M&G code enabling a manufacturing device to create a lens manufacturing component. For purposes of illustration, the process depicted in FIG. 7 is described within the context of a lens mold insert to be manufactured, e.g., a power insert for a front curve lens mold; however, it is understood that the flow depicted in FIG. 7 is generally applicable for generating code for manufacturing other components. As shown in FIG. 5, a first step 502 is to initialize variables used for subsequent calculations. At step 506, the user specifies a directory location where the template data files associated with the lens mold insert to be designed are located. Then, at step 512, there is implemented the step of calling the program that runs macros for producing the M&G code (hereinafter "G Code"). Then, at step 516, there is depicted the step of specifying an input name of a text file to generate tool paths. That is, the user is prompted to enter the file name for the tool path generation. At the next step 518, a directory location where the G Code files are to be located is set, and, at step 522, the user is prompted to set the data file name to read for tool path generation. The steps 525, 530 depict the actual looping through the data file to read in all values. This step utilizes the "DimDump" macro described herein for returning all driving dimensions (and reference dimensions) for the geometries of the part being manufactured. Then, at step 535, a decision is made to determine if other tool paths are needed. For example, in the context of lens mold inserts, two tooling paths are implemented, a first "rough" tooling path and a "finishing" path. For some manufactured products, if only a first tooling path is required, then the flow may branch to generate CNC code, for example, at step 535. Otherwise, in the context of lens mold power insert, the process proceeds to step 537 where all geometry starting at an edge is created and the G Code output generated. At step 540, all edge detail G Code is written to the specified G Code files. Next, at step 546, in accordance with generating G Code for lens mold inserts, there is performed the steps of calculating "fillet" points and to perform the mathematics for the finish geometry. Then, in the context of generating G Code for lens mold inserts there is next implemented the step 550 of looping through front zone data to create arcs. Then at step 560 and 567, after the data and geometries have been read, the output G code is generated and sent to the specified G file. When a manufacturing machine including diamond point turning is implemented, the sample G Code generated according to the process depicted in FIG. 7 will generate code, such as the example G Code shown in Table 1.

TABLE 1

| |
|---|
| G02 X5.yyyyyy Z0 |
| G01 X5.yyyyyy Z0.zzzzzz R0.xxxxx |
| G03 X5.yyyyyy Z0.zzzzzz |
| G02 X5.yyyyyy Z0.zzzzzz.xxxxxx |
| G03 X5.yyyyyy Z0.zzzzzz R8.xxxxxx |

As is known, G codes are preparatory commands and M codes are miscellaneous commands. The G file programs are programs made up of commands, and commands are made up of words. Each word has a letter address and a numerical value. The letter address informing the control system of the word type. The CNC control manufacturers do vary with regard to how they determine word names (letter addresses) and their meanings. The beginning CNC programmer must reference the control manufacturer's programming manual to determine the word names and meanings. Some of the word types and their common letter address specifications, are as follows:

O—Program number (Used for program identification)
N—Sequence number (Used for line identification)
G—Preparatory function
X—X axis designation
Y—Y axis designation
Z—Z axis designation
R—Radius designation
F—Feedrate designation
S—Spindle speed designation
H—Tool length offset designation
D—Tool radius offset designation
T—Tool Designation
M—Miscellaneous function (See below)

As is understood, there are two letter addresses (G and M) that allow special functions to be designated. The preparatory function (G) specifies is commonly used to set modes. However, the control manufacturer's manual must be consulted to find the list of preparatory functions for the particular machine. Like preparatory functions, miscellaneous functions (M words) allow a variety of special functions. Miscellaneous functions are typically used as programmable switches (like spindle on/off, coolant on/off, and so on). They are also used to allow programming of many other programmable functions of the CNC machine tool. Further information regarding the generation of G&M code and explaining word commands thereof, may be found by referencing a web-site entitled Fundamentals of CNC http://www.seas.upenn.edu/~meam100/cnc/cnc$_{13}$ main.html, the contents and disclosures of which are incorporated by reference as if fully disclosed herein.

As more and more templates are created, in effect, a catalogue of templates is developed for storage in the database 60 (FIG. 1). These are re-used for producing tooling designs where the lens design to be used as input is similar to what the original template was designed for. The tool provides enhancements to the template building methodology, the software applications that modify the template functionality and output, and data output formatting. Modifications to the structure are also frequent—with the tool used to improve efficiency.

The use of 3D CAD/CAM modeling software tools provides the advantage of data management control systems. Once designs are created and properly renamed (to follow an agreed nomenclature), parts can be checked into a library of designs that can be accessed by the tool designers to read, modify or copy. It is understood that permission levels may be set to allow or limit access to the checked-in parts. Tooling design iterations are tracked this way.

The use of commercially available 3D CAD/CAM modeling software additionally provides the ability to import and export part designs to other CAD platforms and generic software packages. This allows, for instance, checking lens molds against production line handling equipment (suction cups, de-mold fingers etc) designed with other 3D CAD/CAM modeling software, for fit and interference verification. The 3D CAD/CAM modeling software also allows for exporting the lens, lens mold and insert geometries to be used in analysis applications, such as mechanical and thermal finite-element analysis.

Moreover, the use of 3D CAD/CAM modeling software enables the 100% accurate modeling of data. It is additionally much easier to use relationships between lenses, molds and inserts that are orders of magnitude more complex than previously allowed, because of the power of NURBS and the "point and click" system, when rendered accessible to those authorized users, and its associated database of accurate up-to-date information reduces any communication inadequacies and helps reduce the Design-Build-Test Cycle, from concept through to the calibration, scale-up and manufacturing processes.

It should be understood that, when it is decided to pursue a new market opportunity, for example, a new lens design, more efficient communication between the marketing and related design functions is achieved using 3D CAD/CAM modeling software and use of associated modeled components helps reduce the interaction time and improve productivity. This tool is also available to promote the New Products, linking directly back to the design and manufacturing processes, if needed. The 3D models are invaluable in assessing new marketing opportunities and technical challenges for new product development or line-extensions. This reduces communication errors, reduces the DBT cycle and provides designers with tools to better predict the performance of these products in the marketplace.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

The invention claimed is:

1. An ophthalmic lens design and modeling system comprising:
    a) means for generating a user interface display device providing functionality for generating a template associated with a desired lens design to be manufactured, said template comprising design information sufficient for generating three-dimensional (3D) models of the lens, and 3D models of associated components comprising at least one of: a lens mold, an insert and a core;
    b) means for generating a 3D model of the lens and the associated components;
    c) means for receiving data descriptive of a change of a manufacturing process parameter based upon data descriptive of operating conditions of a manufacturing line, said process parameter comprising at least one of: shrinkage of plastic from an insert and hydration of contact lens monomer;
    d) means for generating linking information for governing the lens design information included in said template in accordance with one or more of: process parameters affecting lens manufacture and parameters affecting manufacture of the associated components;
    e) means for modifying design information via the linking information and based upon the data descriptive of a change in a manufacturing process parameter;
    f) means for generating a revised 3D model of the lens and the associated components, based upon the modified design information; and
    g) means for utilizing lens design data and said linking information from said template for driving lens manufacture of the associated lens design in an ophthalmic lens manufacturing system.

2. The system as claimed in claim 1, further comprising:
    a) memory storage means for storing templates that have been generated, said user interface mean is providing functionality for accessing a stored templates;
    b) editing means enabling a user to modify one of: lens, lens mold, mold insert, template design information and linking information provided with a the stored template; and
    c) means for automatically generating a new 3D model of a lens, lens mold, and mold insert, each 3D model automatically based upon the modified lens, lens mold, mold insert, template design information or linking information, wherein said memory storage means a catalogue of developed templates that may be accessed and re-used for producing new lens designs.

3. The system as claimed in claim 2, wherein said means generating a user interface display provides functionality for specifying expansion and shrinkage factors associated with manufacture of said lens design as performed by said ophthalmic lens manufacturing system, whereby specified changes to said factors are automatically reflected in resultant 3D models generated.

4. The system as claimed in claim 3, wherein a template further comprises manufacturing data associated with a lens design including machining data and engineering drawings, said manufacturing data available as direct input to an ophthalmic lens manufacturing system for driving the lens manufacturing process necessary to achieve a particular lens design.

5. The system as claimed in claim 4, wherein associated manufacturing components for said lens include one or more lens mold and mold inserts used in lens mold manufacture, said template further comprising manufacturing data for enabling manufacture of one or more lens mold according to lens mold designs associated with a particular lens design, and, manufacture of mold inserts according to mold insert designs, each said lens mold and lens mold design accounting for process parameter variations by specified linking information.

6. The system as claimed in claim 4, wherein said lens design information comprises one or more of: a text file or electronic data representing an output of a three-dimensional computer aided design (CAD) system.

7. The system as claimed in claim 5, wherein said functionality for generating a template associated with a desired lens via said user interface includes means for importing lens design information into said template, and generating a 3D lens models for visual presentation via said user interface.

8. The system as claimed in claim 5, wherein a 3D CAD/CAM modeling software is Non-Uniform Rational B-Spline (NURB)-based, obviating the need for programmers to write lines of computer code for the lens, lens mold and insert designs, and assemblies.

9. The system as claimed in claim 5, further comprising means for automatically generating manufacturing data from said template, said generated data being directly input to an ophthalmic lens manufacturing system for driving the lens manufacturing and component build process necessary to achieve the associated lens design.

10. An ophthalmic lens design and modeling system comprising:
  a) means generating a user interface display device providing functionality for generating a template associated with a desired lens design to be manufactured, said template comprising design information sufficient for generating three-dimensional (3D) models of lens, and 3D models of associated components required for lens manufacture in an ophthalmic lens manufacturing system and wherein said means generating a user interface display device provides functionality for specifying expansion and shrinkage factors associated with manufacture of said lens design as performed by said ophthalmic lens manufacturing system, whereby specified changes to said factors are automatically reflected in resultant 3D models generated, wherein a template comprises manufacturing data associated with a lens design including machining data and engineering drawings, said manufacturing data available as direct input to an ophthalmic lens manufacturing system for driving the lens manufacturing process necessary to achieve a particular lens design and wherein associated manufacturing components for said lens include one or more lens mold and mold inserts used in lens mold manufacture, said template further comprising manufacturing data for enabling manufacture of one or more lens mold according to lens mold designs associated with a particular lens design, and, manufacture of mold inserts according to mold insert designs, each said lens mold and lens mold design accounting for process parameter variations by specified linking information;
  b) means generating linking information for governing physical behavior of lens design features included in said template in accordance with one or more process parameters affecting lens manufacture and manufacture of associated components in an ophthalmic lens manufacturing system;
  c) means for utilizing lens design data and said linking information from said template for driving lens manufacture of the associated lens design in an ophthalmic lens manufacturing system, wherein use of said template and design and linking information therein facilitates rapid lens modeling and lens manufacturing operations with greater accuracy, thereby reducing lens design build and test (DBT) cycle time, wherein said lens design data comprises one or more of: text file or an electronic file representing an output of a three-dimensional computer aided design (CAD) system;
  d) memory storage means for storing templates that have been generated, said use interface means providing functionality for accessing stored templates; and
  e) editing means enabling a user to modify lens, lens mold, mold insert, template design information and linking information provided with a template to create a new lens, lens mold, mold insert, template design, said memory storage means defining a catalogue of developed templates that may be accessed and re-used for producing new lens designs wherein said lens design information comprises one or more equations utilizing process parameters that govern lens manufacturing operating conditions, said equations provided for linking the lens design with the manufacture of a back curve (BC) lens mold; linking the lens design with the manufacture of a front curve (FC) lens mold; and, linking the manufacture of a BC and FC lens mold with a resultant physical lens mold assembly, and then the insert pair designs of BC and rear core insert, and FC and front core design;
  wherein said lens design information comprises one or more equations utilizing process parameter is that govern lens manufacturing operating conditions, said equations provided for: linking the lens design with the manufacture of a back curve (BC) lens mold; linking the lens design with the manufacture of a front curve (FC) lens mold; and, linking the manufacture of a BC and FC lens mold with a resultant physical lens mold assembly, and then the insert pair designs of BC and rear core insert, and FC and front core design.

11. A method for designing and modeling ophthalmic contact lenses comprising the steps of:
  a) generating a user interface display device providing functionality for generating a template associated with a desired lens design to be manufactured, said template comprising design information sufficient for generating three-dimensional (3D) models of lens, and 3D models of associated components comprising at least one of: a lens mold an insert and a core
  b) generating a 3D model of the lens and the associated components;
  c) receiving data descriptive of a change of a manufacturing process parameter based upon data descriptive of operating conditions of a manufacturing line, said process parameter comprising at least one of: shrinkage of plastic from an insert and hydration of contact lens monomer;
  d) generating linking information for governing physical behavior of lens design information included in said template in accordance with one or more process parameters affecting lens manufacture and manufacture of associated components in an ophthalmic lens manufacturing system;
  e) modifying design information via the linking information and based upon the data descriptive of a change in a manufacturing process parameter;
  f) generating a revised 3D model of the lens and the associated components, based upon the modified design information; and
  g) utilizing lens design data and said linking information from said template for driving lens manufacture of the associated lens design in an ophthalmic lens manufacturing system.

12. The method as claimed in claim 11, further comprising the steps of:
  storing each template that has been generated, said user interface display providing functionality for accessing stored templates;
  modifying one of: lens, lens mold, insert and template design information and linking information provided with a stored template; and automatically generating a new 3D model of a lens: lens mold, and mold insert, each 3D model automatically based upon the modified lens, lens mold, mold insert, template design information or linking information, wherein said memory storage means a catalogue of developed templates that may be accessed and re-used for producing new lens designs.

13. The method as claimed in claim 12, wherein said generated user interface display device provides functionality for specifying expansion and shrinkage factors associated with manufacture of said lens design as performed by said ophthalmic lens manufacturing system, whereby specified changes to said factors are automatically reflected in resultant 3D models generated.

14. The method as claimed in claim 13, wherein a template further comprises manufacturing data associated with a lens design, said method including the step of directly inputting manufacturing data available from said template to an ophthalmic lens manufacturing system for driving the lens manufacturing process necessary to achieve a particular lens design.

15. The method as claimed in claim 14, wherein associated manufacturing components for said lens include one or more lens mold and mold inserts used in lens mold manufacture, said method further including: utilizing manufacturing data in said template for enabling manufacture of one or more lens mold according to lens mold designs associated with a particular lens design, and, manufacture of mold insert according to mold insert designs, each said lens mold and lens mold design accounting for process parameter variations by specified linking information.

16. The method as claimed in claim 14, wherein said lens design information comprises one or more of: text file or an electronic file representing an output of a three-dimensional computer aided design (CAD) system.

17. The method as claimed in claim 15, wherein said step of generating a template comprises associated with a desired lens via said user interface includes the step of: importing lens design information into said template, and generating a 3D lens models for visual presentation via said user interface.

18. The method as claimed in claim 15, wherein said user interface display comprises 3D modeling software that is Non-Uniform Rational B-Spline (NURB)-based, obviating the need for programmers to write lines of computer code for the lens, lens mold and insert designs.

19. The method as claimed in claim 15, further including the step of: automatically generating manufacturing data from said template, said generated data being directly input to an ophthalmic lens manufacturing system for driving the lens manufacturing and associated component build processes necessary to achieve the associated lens design.

20. The method as claimed in claim 19, wherein said manufacturing data available as direct input to an ophthalmic lens manufacturing system includes computer numeric control (CNC) data.

21. The method as claimed in claim 19, wherein said manufacturing data available as direct input to an ophthalmic lens manufacturing system includes M&G data.

22. A method for designing and modeling ophthalmic contact lenses comprising the steps of:

a) generating a user interface display device providing functionality for generating a template associated with a desired lens design to be manufactured, said template comprising design information sufficient for generating three-dimensional (3D) models of lens, and 3D models of associated components required for lens manufacture in an ophthalmic lens manufacturing system, wherein associated manufacturing components for said lens include one or more lens mold and mold inserts used in lens mold manufacture, said method further including; utilizing manufacturer data in said template for enabling manufacture of one or more lens mold according to lens mold designs associated with a particular lens design, and, manufacture of mold insert according to mold insert design, each said lens mold and lens mold design accounting for process parameter variations by specified linking information and wherein said generated user interface display device provides functionality for specifying expansion and shrinkage factors associated with manufacture of said design as performed by said ophthalmic lens manufacturing system, whereby specified changes to said factors are automatically reflected in resultant 3D models generated and wherein a template comprises manufacturing data associated with a lens design, said method including the step of directly inputting manufacturing data available from said template to an ophthalmic lens manufacturing system for driving the lens manufacturing process necessary to achieve a particular lens design;

b) generating linking information for governing physical behavior of lens design features included in said template in accordance with one or more process parameters affecting lens manufacture and manufacture of associated components in an ophthalmic lens manufacturing system;

c) utilizing lens design data and said linking information from said template for driving lens manufacture of the associated lens design in an ophthalmic lens manufacturing system, wherein use of said template and design and linking information therein facilitates rapid lens modeling and lens manufacturing operations with greater accuracy, thereby reducing lens design build and test (DBT) cycle time; and d) storing each template that has been generated, said user interface display providing functionality for accessing stored templates; and, modifying or editing lens, lens mold, insert and template design information and linking information provided with a template to operate a new lens design, said memory storage means defining a catalogue of developed templates that may be accessed and re-used for producing new lens designs;

wherein said lens design information comprises one or more equations utilizing process parameters that govern lens manufacturing operating conditions, said equations provided for: linking the lens design with the manufacture of a back curve (BC) lens mold; linking the lens design with the manufacture of a front curve (FC) lens mold; and, linking the manufacture of a BC and FC lens mold with a resultant physical lens mold assembly, and then the insert pair designs of BC and rear core insert, and FC and front core design.

23. A program storage device readable by a machine, tangibly embodying a program of instructions executable by the machine to perform method steps for designing and modeling ophthalmic contact lenses, said method comprising the steps of, a) generating a user interface display device providing functionality for generating a template associated with a desired lens design to be manufactured, said template comprising design information sufficient for generating three-dimensional (3D) models of lens, and 3D models of associated components comprising at least one of: a lens mold, an insert and core;

b) generating a 3D model of the lens and the associated components;

c) receiving data descriptive of a change of a manufacturing process parameter based upon data descriptive of operating conditions of a manufacturing line, said process parameter comprising at least one of: shrinkage of plastic from an insert and hydration of contact lens monomer;

generating linking information for governing lens design information included in said template in accordance with one or more process parameters affecting lens manufacture and parameter affecting manufacture of the associated components in an ophthalmic lens manufacturing system;

e) utilizing lens design data and said linking information from said template for driving lens manufacture of the associated lens design in an ophthalmic lens manufacturing system, wherein use of said template and design and linking information therein facilitates rapid lens modeling and lens manufacturing operations with greater accuracy, thereby reducing lens design build and test (DBT) cycle time e) modifying design information via the linking information and based upon the data descriptive of a change in a manufacturing process parameter;

f) generating a revised 3D model of the lens and the associated components, based upon the modified design information; and g) utilizing lens design data and said linking information from said template for driving lens manufacture of the associated lens design in an ophthalmic lens manufacturing system.

24. The program storage device readable by a machine as claimed in claim 23, wherein said method further comprises the steps of: storing each template that has been generated, said user interface display providing functionality for accessing stored template; and, modifying or editing lens, lens mold, mold insert and template design information and linking information provided with a template to create a new lens, lens mold, mold insert and template design, said memory storage means defining a catalogue of developed templates that may be accessed and re-used for producing new lens designs.

25. The program storage device readable by a machine as claimed in claim 23, wherein said generated user interface display device provides functionality for specifying expansion and shrinkage factors associated with manufacture of said lens design as performed by said ophthalmic lens manufacturing system, whereby specified changes to said factors are automatically reflected in resultant 3D models generated.

26. The program storage device readable by a machine as claimed in claim 25, wherein said method further comprises the step of: automatically generating manufacturing data from said template, said generated data functioning as direct input to an ophthalmic lens manufacturing system for driving the lens manufacturing and associated component build processes necessary to achieve the associated lens design.

27. The program storage device readable by a machine as claimed in claim 26, wherein said associated manufacturing components for said lens one or more lens mold and mold inserts used in lens mold manufacture, said method further including: utilizing said generated manufacturing data to enable manufacture of one or more lens molds according to lens mold designs associated with a particular lens design, and, manufacture of mold inserts according to mold insert designs, each said lens mold and lens mold design accounting for process parameter variations by specified linking information.

28. An ophthalmic lens design system comprising
a) means generating a user interface display device providing functionality for designing an ophthalmic contact lens and associated components required for manufacture of that lens by an ophthalmic lens manufacturing system and generating design information that is stored in a database accessible by a user via said interface;

b) means for automatically generating a three-dimensional (3D) model of said ophthalmic contact lens and models of each of associated components required for manufacture of that lens, and displaying said 3D model via said user interface;

c) means for manipulating said 3D models via said user interface for modifying lens design features and features of associated components required for manufacture of that lens design as required for optimizing said lens design;

d) means for automatically updating design information of the lens and the all of associated components based upon the manipulation of a 3-D model of one or more of the lens and the components;

d) means for generating lens design data and data governing design of associated components thereof for storage in said database, and automatically updating data as said 3D models of said lens design and associated components are manipulated by said user; and, e) means capable of automatically generating manufacturing data from said stored data, said generated data functioning as direct input to said ophthalmic lens manufacturing system for driving the lens manufacturing and associated component build processes necessary to achieve the associated lens design, wherein modeling and lens manufacturing operations are performed with greater accuracy in less time.

29. The system as claimed in claim 28, further comprising: means for generating linking information governing physical behavior of lens design features in accordance with one or more process parameters affecting lens manufacture and manufacture of said associated components in said ophthalmic lens manufacturing system.

30. The system as claimed in claim 29, wherein said associated components include: lens mold and mold insert associated with manufacture of a particular lens design.

31. The system as claimed in claim 30, further comprising means for generating a template structure for receiving said lens design and linking information required to create a lens and associated lens mold and mold inserts and, storing said templates in said database means, wherein a plurality of developed templates are stored for user access and may be re-used for generating new lens designs.

32. The system as claimed in claim 31, wherein said means generating a user interface display device provides functionality for specifying expansion and shrinkage factors associated with manufacture of said lens design as performed by said ophthalmic lens manufacturing system, whereby specified changes to said factors are automatically reflected in resultant 3D models generated.

33. The system as claimed in claim 32, further comprising means for automatically generating manufacturing data from said template, said generated data functioning as direct input to an ophthalmic lens manufacturing system for driving the lens manufacturing and associated component build processes necessary to achieve the associated lens design.

34. The system as claimed in claim 33, wherein said associated manufacturing components far said lens include one or more lens mold and mold inserts used in lens mold manufacture, said method further including: utilizing said generated manufacturing data to enable manufacture of one or more lens molds according to lens mold designs associated with a particular lens design, and, manufacture of mold inserts according to mold insert designs, each said lens mold and lens mold design accounting for process parameter variations by specified linking information.

* * * * *